United States Patent [19]

Grier et al.

[11] 4,273,781
[45] Jun. 16, 1981

[54] TREATMENT OF PAIN, FEVER, AND INFLAMMATION WITH COMPOSITIONS CONTAINING PIPERIDINOBUTAN-AND 3-BUTEN-2-ONES

[75] Inventors: Nathaniel Grier, Englewood; Richard A. Dybas, Somerville; Bruce E. Witzel, Rahway, all of N.J.

[73] Assignee: Merck & Co., Inc., Rahway, N.J.

[21] Appl. No.: 169,566

[22] Filed: Jul. 17, 1980

Related U.S. Application Data

[62] Division of Ser. No. 59,404, Jul. 20, 1979.

[51] Int. Cl.$^3$ .......................................... A61K 31/445
[52] U.S. Cl. .................................................. 424/267
[58] Field of Search ........................................ 424/267

[56] References Cited
U.S. PATENT DOCUMENTS 4,145,426   3/1979   Grier et al. ........................ 424/267

*Primary Examiner*—Stanley J. Friedman
*Attorney, Agent, or Firm*—Theresa Y. Cheng; Raymond M. Speer; Mario A. Monaco

[57] ABSTRACT

A method of treating pain, fever, and inflammation and pharmaceutical compositions for use therein, wherein the active ingredient comprises a compound of the formula;

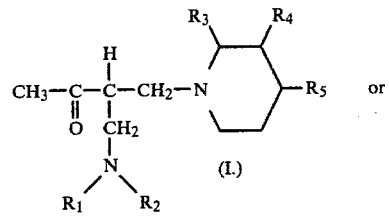

(I.)

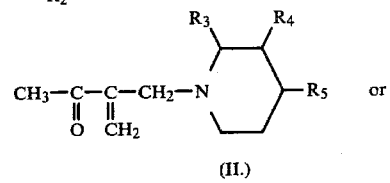

(II.)

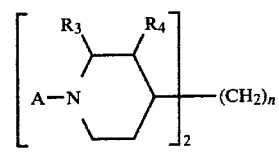

(III.)

6 Claims, No Drawings

TREATMENT OF PAIN, FEVER, AND INFLAMMATION WITH COMPOSITIONS CONTAINING PIPERIDINOBUTAN-AND 3-BUTEN-2-ONES

This is a division of application Ser. No. 059,404, filed July 20, 1979.

BACKGROUND OF THE INVENTION

1. Field of the Invention

The present invention is concerned with certain novel compounds, and with a novel method of treating pain, fever, and inflammation and novel compositions for use therein containing as an active ingredient, a piperidinobutan- or 3-buten-2-one compound.

2. Brief Description of the Prior Art

Various piperidinobutan-and 3-buten-2-ones used in the method and compositions of the present invention are disclosed in U.S. Pat. No. 4,145,426 and Dybas et al, *Development in Industrial Microbiology*, Vol. 19, pp. 347–353 (1978). However, they are described therein as being useful in a process for protecting materials of various kinds against infection and damage by microorganisms, as by bacteria and fungi, and, thus, the method and compositions of the present invention are not suggested.

SUMMARY OF THE INVENTION

The present invention provides novel compounds of the formula:

$$\left[ A-N \underset{\underset{2}{\diagup}}{\overset{R_3 \quad R_4}{\diagdown}} (CH_2)_n \right]_2 \quad (III.)$$

wherein $R_3$ and $R_4$ are selected from hydrogen; $C_{1-3}$ alkyl; $C_{2-3}$ alkenyl; hydroxy; hydroxy $C_{1-3}$ alkyl; phenyl; carboxyl; carboxamido; $C_{1-4}$ N-mono- and N,N-disubstituted carbonylamino; $C_{1-4}$alkoxycarbonyl; 1-pyrrolidinyl; and 1-piperidinyl;

A is $$CH_3-\underset{\underset{O}{\|}}{C}-\underset{\underset{CH_2-N \diagdown R_2}{\diagup R_1}}{CH}-CH_2- \quad \text{or} \quad CH_3-\underset{\underset{O}{\|}}{C}-\underset{\underset{CH_2}{\|}}{C}-CH_2-;$$

and n is 0 to 3; and acid addition and quaternary salts thereof.

An example of a preferred compound of the present invention is 3,3'-[1,3-propanediylbis-(4,1-piperidinediyl)-bis(methylene)]bis[3-buten-2-one].

In accordance with the present invention there is also provided a method of treating pain, fever, and inflammation comprising administering to a host in need of such treatment a therapeutically effective amount of a compound of the formula:

$$CH_3-\underset{\underset{O}{\|}}{C}-\underset{\underset{\underset{R_1 \diagup \diagdown R_2}{N}}{CH_2}}{\overset{H}{C}}-CH_2-N\underset{\diagdown \quad \diagup}{\overset{R_3 \quad R_4}{\diagdown}} R_5 \text{ or} \quad (I.)$$

$$CH_3-\underset{\underset{O}{\|}}{C}-\underset{\underset{CH_2}{\|}}{C}-CH_2-N\underset{\diagdown \quad \diagup}{\overset{R_3 \quad R_4}{\diagdown}} R_5 \text{ or} \quad (II.)$$

$$\left[ A-N \underset{\underset{2}{\diagup}}{\overset{R_3 \quad R_4}{\diagdown}} (CH_2)_n \right]_2 \quad (III.)$$

wherein $R_1$ and $R_2$ are independently selected from hydrogen; $C_{1-8}$ alkyl; $C_{2-8}$ alkenyl; hydroxy $C_{1-8}$ alkyl; and cyclo $C_{4-8}$ alkyl; or $R_1$ and $R_2$ taken together with the nitrogen atom form a five- or six-membered saturated heterocyclic ring substituted at the 2-, 3-, and 4-position with $R_3$, $R_4$, and $R_5$, respectively;

$R_3$, $R_4$, and $R_5$ are selected from hydrogen; $C_{1-3}$ alkyl; $C_{2-3}$ alkenyl; hydroxy; hydroxy $C_{1-3}$ alkyl; phenyl; carboxyl; carboxamido; $C_{1-4}$ alkyl N-mono- and N,N-disubstitutedcarbonylamino; $C_{1-4}$ alkoxycarbonyl; 1-pyrrolidinyl; and 1-piperidinyl;

A is $$CH_3-\underset{\underset{O}{\|}}{C}-\underset{\underset{CH_2-N \diagdown R_2}{\diagup R_1}}{CH}-CH_2- \quad \text{or} \quad CH_3-\underset{\underset{O}{\|}}{C}-\underset{\underset{CH_2}{\|}}{C}-CH_2-;$$

and n is 0 to 3; and acid addition and quaternary salts thereof.

Examples of preferred compounds for use in the novel pharmaceutical compositions and method of treatment of the present invention are:

3-(1-piperidinylmethyl)-3-buten-2-one;
4-(4-hydroxy-1-piperidinyl)-3-[(4-hydroxy-1-piperidinyl)methyl]buten-2-one
3,3'-[1,3-propanediylbis(4,1-piperidinediyl) bis(methylene)]bis[3-buten-2-one]
3-[(3-carbamylpiperidino)methyl]-4-(3-carbamylpiperidino)butan-2-one adipate
3-[(4-carboxypiperidino)methyl]-4-(4-carboxypiperidino)butan-2-one
3-[(3-hydroxymethylpiperidino)methyl]-4-(3-hydroxymethylpiperidino)buten-2-one The present invention also provides pharmaceutical compositions for treating a condition exhibiting at least one of the symptoms of pain, fever, and inflammation, comprising a pharmaceutically acceptable, non-toxic carrier, and a therapeutically effective amount of a compound of Formulas I, II, or III as described above.

The compounds of Formula I useful in the method and compositions of the present invention may be synthesized by techniques involving the condensation of 2-, 3-, or 4-substituted piperidines, formaldehyde, and acetone, as illustrated in the following reaction scheme:

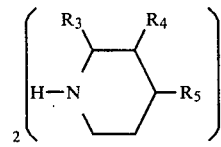

A.

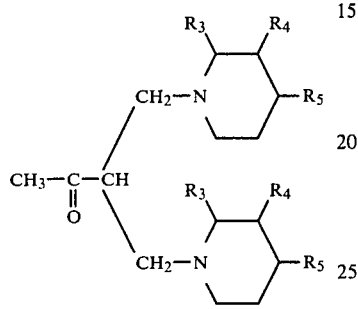

The olefinic elimination products of Formula II may be obtained from the compounds synthesized by the procedures shown in A. above, using a variety of methods such as with heat, salt formation with oxalic acid, by steam distillation to cite some, as illustrated in the following reaction scheme:

B.

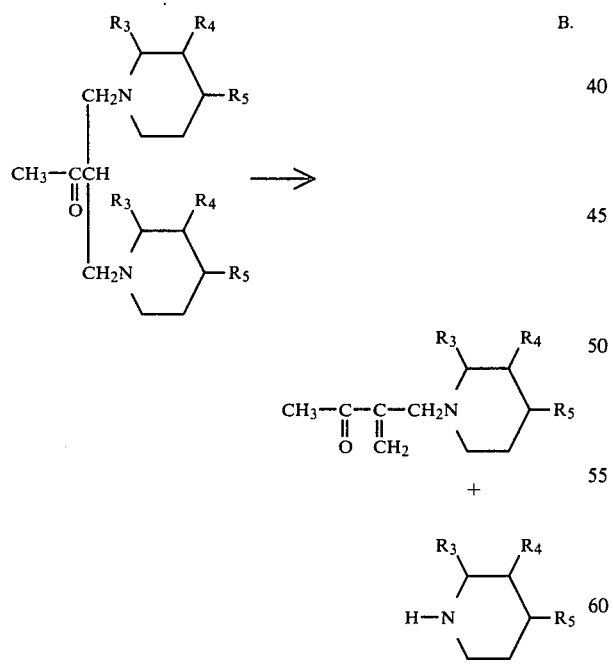

Several routes are suitable for the synthesis of the compounds of Formula I wherein the two base substituents are different. The mono-Mannich base may be prepared as follows:

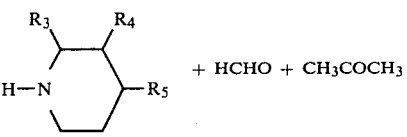

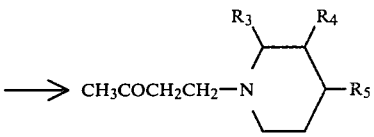

and reacted with a second mole of formaldehyde and secondary amine:

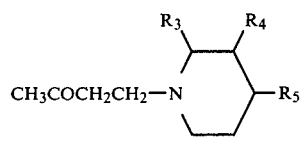

A mole of amine may be added to the olefin of Formula II:

Or, the various sequences outlined may employ the secondary amine, initially to produce the bis-Mannich derivative. Elimination of one mole of amine then provides the following compounds:

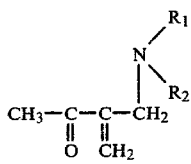

Addition of one mole of

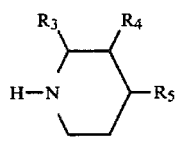

forms compounds of Formula I.

The compounds of Formula I which contain identical substituted piperidine groups are prepared by reacting substantially molar ratios of 2:1:2 with respect to amine, acetone and formaldehyde. A considerable excess of the first and/or third reaction component may be used.

A variety of solvents may be used for the synthesis including water, alcohols, ethers as well as an excess of one of the reagents other than acetone. The amines can be used in the Mannich reaction as free bases or in the form of salts such as the acetate or hydrochloride. Generally, elevated temperatures are required in the range of 45° C. to 110° C. and reaction periods of from 1 to 24 hours. Isolation of products may be accomplished by crystallization or distillation. Any other chemical groupings present in the organic bases employed for the Mannich reaction which contain active hydrogen should preferably be blocked and afterwards liberated by techniques well known in the art.

The addition reactions of Formula II olefinic compounds with amines to provide Formula I derivatives may be run with a 1:1 molar ratio of reactants in solvents such as water, alcohols, dioxane or mixtures of these or neat. Generally, no heat is required and reaction times may range from ½ to 10 hours. The course of the reaction is readily monitored by measuring the disappearance of the alpha beta unsaturated ketonic moiety as with ultraviolet or infra-red spectral analysis.

The compounds of Formula III may be prepared in accordance with the procedures described above for preparing the compounds of Formulas I and II, substituting for the piperidines employed therein, the appropriate dipiperidine compound.

Both Formula I and Formula II compounds can be used in the form of salts derived from inorganic or organic acids. Included among such salts are the following: acetate, adipate, alginate, aspartate, benzoate, benzenesulfonate, bisulfate, butylrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The piperidinobutan-and 3-buten-2-ones of the present invention possess a high degree of anti-inflammatory, analgesic and anti-pyretic activity. They are of value in the treatment of arthritic and dermatological disorders or like conditions responsive to anti-inflammatory drugs. In general they are indicated for a wide variety of conditions where one or more of the symptoms of inflammation, fever and pain are manifested. Included within this category are diseases such as rheumatoid arthritis, osteo arthritis, gout, infectious arthritis and rheumatic fever. As indicated above the compounds utilized in the practice of the invention also possess a useful degree of analgesic and anti-pyretic activity.

For these purposes the compounds of the present invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, dogs, cats, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for manufacture of tablets. These excipients may be, for example, inert diluents, such as calcium carbonate, sodium carbonate, lactose, calcium phosphate or sodium phosphate; granulating and disintegrating agents, for example maize starch, or alginic acid; binding agents, for example starch, gelatine or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate alone or with a wax may be employed.

Formulations for oral use may also be presented as hard gelatine capsules wherein the active ingredient is mixed with an inert solid diluent, for example calcium carbonate, calcium phosphate or kaolin, or as soft gelatine capsules wherein the active ingredient is mixed with water or an oil medium, for example arachis oil, peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a natural-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol mono-oleate, or condensation products of ethylene oxide with partial esters derived from fatty acids and hexitol anhydrides, for example polyoxyethylene sorbitan mono-oleate. The said aqueous suspensions may also contain one or more preservatives, for example, ethyl or n-propyl p-hydroxy benzoate, one or more coloring agents, one or more flavoring agents and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents, such as those set forth above, and flavouring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavouring and colouring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The compounds of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc. containing the anti-inflammatory agents are employed.

Dosage levels of the order of 20 mg. to 1 gram per day are useful in the treatment of the above indicated conditions. For example, inflammation is effectively treated and anti-pyretic and analgesic activity manifested by the administration of from about 0.3 to 60 milligrams of the compound per kilogram of body weight per day. Advantageously from about 2 mg. to about 30 mg. per kilogram of body weight and especially from about 4 mg. to about 20 mg./kg. per daily dosage produce highly effective results.

The amount of active ingredient that may be combined with the carrier materials to produce a single dosage form will vary depending upon the host treated and the particular mode of administration. For example, a formulation intended for the oral administration of humans may contain from 5 mg. to 1 gram of active agent compounded with an appropriate and convenient amount of carrier material which may vary from about 5 to about 95 percent of the total composition. Dosage unit forms will generally contain between from about 25 mg. to about 500 mg. of active ingredient.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The following examples will serve to illustrate preparation of the compounds used in the method of treatment and pharmaceutical compositions of the present invention, without, however, limiting the scope thereof.

EXAMPLE 1

3-[(4-Hydroxypiperidino)methyl]-4-(hydroxypiperidino)-butan-2-one

A solution of 4-hydroxypiperidine (20.5 g.) in 40 ml. of water is chilled in an ice bath and mixed with acetone (30 ml.) and potassium chloride (15.1 g.). After complete solution there is added dropwise over a 15-minute period formaldehyde, aqueous 35% (18 ml.). The reaction mixture was then stirred 12 hr. at 20°–25° C. It was made alkaline with 50% sodium hydroxide aqueous solution and the resultant two phases separated. The aqueous layer was cooled and extracted several times with methylene chloride. The combined organic phase and methylene chloride extracts were washed with saturated sodium chloride solution and then dried over anhydrous sodium sulfate. After filtration the solvent was stripped under reduced pressure leaving an oil, 24.2 g. Its mass spectrum showed a molecular ion of 183, the infrared and nuclear magnetic resonance proton spectra were in agreement for the product.

In place of 4-hydroxypiperidine the following substituted piperidines may be reacted using the above procedure with formaldehyde and acetone to provide the indicated products.

| | Piperidine Substituent | Product |
|---|---|---|
| 1. | 3-Hydroxy | 3-[(3-Hydroxypiperidino)methyl]-4-(3-hydroxypiperidino)butan-2-one |
| 2. | 3-Hydroxymethyl | 3-[(3-Hydroxymethylpiperidino)methyl]-4-(3-hydroxymethylpiperidino)butan-2-one |
| 3. | 4-Carboxy | 3-[(4-Carboxypiperidino)methyl]-4-(4-carboxypiperidino)-butan-2-one |
| 4. | 3-Carbamyl | 3-[(3-Carbamylpiperidino)methyl]-4-(3-carbamylpiperidino)-butan-2-one |
| 5. | 4-(N-Methylcarbamyl) | 3-{[4-(N-Methylcarbamyl)piperidino]methyl}-4-[4-(N-methylcarbamyl)piperidino]butan-2-one |
| 6. | 4-Ethoxycarbonyl | 3-[(4-Ethoxycarbonylpiperidino)methyl]-4-(4-ethoxypiperidino)-butan-2-one |
| 7. | 4-Isopropyl | 3-[(4-Isopropylpiperidino)-methy]-4-(4-isopropyl-piperidino)butan-2-one |
| 8. | 3-Methyl-4-hydroxymethyl | 3-[(3-Methyl-4-hydroxymethylpiperidino)methyl]-4-(3-methyl-4-hydroxymethylpiperidino)butan-2-one |
| 9. | 4-Phenyl-4-hydroxy | 3-[(4-Phenyl-4-hydroxypiperidino)methyl]-4-(4-phenyl-4-hydroxypiperidino)butan-2-one |
| 10. | 4-(Piperidino) | 3-{[4-(Piperidino)piperidino]methyl}-4-[4-(piperidino)-piperidino]butan-2-one |
| | Unsaturated Product | 3-{[4-(Piperidino)piperidino]methyl}-3-buten-2-one |
| 11. | 4-(Pyrrolidino) | 3-{[4-(Pyrrolidino)piperidino]methyl}-4-[4-(pyrrolidino)piperidino]butan-2-one |
| | Unsaturated Product | 3-{[4-(Pyrrolidino)piperidino]methyl}-3-buten-2-one |
| 12. | 2-n-Butylpiperidine | 3-[(2-n-Butylpiperidino)methyl]-4-(2-n-butylpiperidino)butan-2-one |

Di-Hydrochloride of 3-[(4-Hydroxypiperidino)methyl]-4-(4-hydroxypiperidino)-butan-2-one The title ketone (2.84 g., 0.01 mole) is dissolved in 50 ml. of dry ether and reacted with dry hydrogen chloride until no further precipitation. The product after aging in the mother liquor is separated, washed with ether and dried at 40° C. under reduced pressure.

EXAMPLE 2

3-[(4-Hydroxypiperidino)methyl]-3-buten-2-one

3-[(4-Hydroxypiperidino)methyl]-4-(4-(hydroxypiperidino)butan-2-one (1 g.) was dissolved in 8 ml. of ethyl alcohol and added to a cooled solution of oxalic acid anhydrous (0.9 g.) in 5 ml. of ethyl alcohol. After standing at 0° C. for five minutes, the resultant precipitate was filtered. The filtrate was stripped of solvent under reduced pressure and the residual oil taken up in a small volume of water, saturated with potassium carbonate and then extracted with ether. The ether solution was dried over anhydrous sodium sulphate, filtered and the filtrate stripped of ether. The residual oil, approximately 0.1 g., was characterized including a proton nuclear magnetic resonance spectrum in deuterated dimethylsulfoxide. There were two vinylic protons, at 5.9 and 6.1 ppm downfield from the reference tetramethylsilane.

Additional 3-[substituted piperidinomethyl]-3-buten-2-ones are prepared by this procedure and include

| Product | Unsaturated Product |
|---|---|
| 3-[(3-Hydroxypiperidino)methyl]-4-(3-hydroxypiperidino)butan-2-one | 3-[(3-Hydroxypiperidino)methyl]-3-buten-2-one |
| 3-[(3-Hydroxymethylpiperidino)methyl]-4-(3-hydroxymethylpiperidino)butan-2-one | 3-[(3-hydroxymethylpiperidino)methyl]-3-buten-2-one |
| 3-[(4-Carboxypiperidino)methyl]-4-(4-carboxypiperidino)butan-2-one | 3-[(4-Carboxypiperidino)methyl]-3-buten-2-one |
| 3-[(3-Carbamylpiperidino)methyl]-4-(3-carbamylpiperidino)butan-2-one | 3-[(3-Carbamylpiperidino)methyl]-3-buten-2-one |
| 3-{[4-(N-methylcarbamyl)-piperidino]methyl}-4-[4-(N-methylcarbamyl)piperidino]butan-2-one | 3-{[4-(N-Methylcarbamyl)piperidino]methyl}-3-buten-2-one |
| 3-[(4-Ethoxycarbonylpiperidino)methyl]-4-(3-ethoxypiperidino)butan-2-one | 3-[(4-Ethoxycarbonylpiperidino)methyl]-3-buten-2-one |
| 3-[(4-Isopropylpiperidino)methyl]-4-(4-isopropylpiperidino)butan-2-one | 3-[(4-Isopropylpiperidino)methyl]-3-buten-2-one |
| 3-[(3-Methyl-4-hydroxymethylpiperidino)methyl]-4-(3-methyl-4-hydroxymethylpiperidino)butan-2-one | 3-[(3-Methyl-4-hydroxymethylpiperidino)methyl]-3-buten-2-one |
| 3-[(4-Phenyl-4-hydroxypiperidino)methyl]-4-(4-phenyl-4-hydroxypiperidino)-butan-2-one | 3-[(4-Phenyl-4-hydroxypiperidino)methyl]-3-buten-2-one |

Methiodide Quaternary Salt of 3-[(4-hydroxypiperidino)methyl]-3-buten-2-one

The olefinic basic ketone (1.83 g., 0.01 mole) is dissolved in 25 ml. of dry ether and mixed with 0.7 ml. of methyl iodide. After stirring overnight an additional 1 ml. of methyl iodide is added and an additional 12 hr. of reaction time is employed. The separated product is washed repeatedly with dry ether and dried.

Benzyl Bromide Quaternary Salt

The basic ketone (1.83 g., 0.01 mole) is dissolved in 15 ml. of acetone and mixed by benzyl bromide (1.9 g., 0.011 mole). The solution is heated in a bath at 70° C. for 12 hr. The solid product is separated, washed with acetone followed by ether and then dried at 45° C. under vacuum.

EXAMPLE 3

3-Diethylaminomethyl-4-(4-hydroxypiperidino)butan-2-one

Step A. 1,1-Bis(Diethylaminomethyl)acetone

This compound was prepared in the manner described in J.A.C.S. 65, 972 (1943) by adding a solution of 210 ml. diethylamine in 400 ml. water to 300 ml. acetone, to which was then added without cooling 170 ml. 37% aqueous formaldehyde solution. The reaction evolved heat, and after standing 16 hours, the 2-phase reaction mixture was made alkaline by the addition of dilute sodium hydroxide, the water phase saturated with sodium chloride and the upper oil phase separated. The brine layer was extracted with three 400 ml. portions of ether; the ether extracts were combined and joined with the oil. The ether solution was dried over magnesium sulphate, and the solvent removed by distillation. The residual oil was fractionated by distillation under reduced pressure to yield the product, b.p. 103°–111°/6 ml.

The reaction was run similarly with the substitution of equimolar quantities of other organic bases in place of diethylamine, namely, dimethylamine, di-n-propylamine, di-isobutylamine, di-2-ethylhexylamine, di-allylamine, piperidine and pyrrolidine. The isolation of the oily reaction product was readily achieved by phase separation. Purification, if desired, could be achieved by fractional distillation or by fractional crystallization of the salts prepared in anhydrous alcohol or ether with inorganic acids. The free bases containing two nitrogen-bearing groups substituted on the one carbon atom of the acetone molecule were high boiling oils of very slight color showing generally low water solubility and being readily soluble in the common organic solvents. Water-saturated solutions showed pH values above 10.

Step B. 3-Diethylaminomethylbut-3-en-2-one

The intermediate olefinic ketone is prepared by the procedure of H. M. E. Carwell [J. Chem. Soc., 1058 (1950)]. The ketone obtained from A., 22.8 g., in 25 ml. of ethanol was added to a solution of 25 g. of anhydrous oxalic acid in 75 ml. of ethanol. The mixture was cooled to 0° C., filtered to remove diethylamine hydrogen oxalate and the mother liquor evaporated to dryness under reduced pressure. The residue was dissolved in a little water, treated with potassium carbonate and extracted with ether. The ether was dried over anhydrous sodium sulphate and the residue obtained by solvent removal was distilled. After re-distillation the product was obtained as an oil, b.p. 82° C./18 mm. Similarly, the other 1,1-bis-(disubstituted aminomethyl)acetones obtained as in A. can be converted to the corresponding 3-disubstituted aminomethylbut-3-en-2-ones. The disubstituted amino term as previously indicated also comprises pyrrolidine and piperidine alicyclic ring analogs. For example, 3-(piperidinomethyl)but-3-en-2-one boils at 135°–139° C./15 mm. and is synthesized following the same procedure from 1,1-bis(-piperidinomethyl)acetone.

The following are synthesized using this procedure:

| Amine + | Unsaturated Product ⟶ | Product |
|---|---|---|
| Dimethylamine | 3-[(3-Hydroxypiperidinomethyl]-3-buten-2-one | 3-Dimethylaminomethyl-4-(3-hydroxypiperidino)butan-2-one |
| Di-n-octyl amine | 3-[(3-Hydroxymethylpiperidino)methyl]-3-buten-2-one | 3-Di-n-octyl-aminomethyl-4-(3-hydroxymethylpiperidino) butan-2-one |
| Ethanol-amine | 3-[(4-carboxypiperidino)methyl]-3-buten-2-one | 3-[(4-carboxy-piperidino)-methyl]-4-(2-amino)butan-2-one |
| Dicyclo-hexylamine | 3-[(3-carbamylpiperidino)methyl]-3-buten-2-one | 3-[(3-carbamyl-piperidino)methyl]-4-(dicyclohexylamino)butan-2-one |
| Pyrrolidine | 3-{[4-(N-methylcarbamyl)piperidino] methyl}-3-buten-2-one | 3-{[4-(N-methylcarbamyl)piperidino]methyl}-4-(pyrrolidino)butan-2-one |
| Piperidine | 3-[(4-ethoxycarbonylpiperidino)methyl]-3-buten-2-one | 3[(4-Ethoxycarbonylpiperidino)methyl]-4-(piperidino)butan-2-one |
| 2-Methyl-piperidine | 3-[(3-Hydroxypiperidino)methyl]-3-buten-2-one | 3-[(2-methyl-piperidino)methyl]-4-(3-hydroxy-piperidino)butan-2-one |
| Diethanol-amine | 3-[(4-Isopropylpiperidino)methyl]-3-buten-2-one | 3-[di-(2-hydroxy-ethyl)aminomethyl]-4-(4-isopropyl-piperidino)butan-2-one |
| n-Hexylamine | 3-[(3-methyl-4-hydroxymethylpiperidino) methyl]-3-buten-2-one | 3-n-Hexylamine-methyl-4-(3-methyl-4-hydroxymethylpiperidino) butan-2-one |
| Cyclopentyl-amine | 3-[(4-Phenyl-4-hydroxypiperidino)methyl-3-buten-2-one | 3-(Cyclopentyl-aminomethyl)-4-(4-phenyl-4-hydroxypiperidino)butan-2-one |

EXAMPLE 4

3,3'-[1,3-Propanediylbis (4,1-piperidinediyl)bis(methylene)]bis[3-buten-2-one]

A cold solution of acetone (3.7 ml.) and 37% aqueous formaldehyde (8.9 g.) was maintained at 4°–6° C., and then over an 8 minute period bis [4,4'-(1,3-trimethylene) dipiperidine (5.26 g.) was added. Concentrated hydrochloric acid (5 ml.) was added dropwise over 20 minutes to the resulting mixture, while the temperature was maintained at 5°–10° C. The resulting solution was warmed to 20° C., stirred for 1 hr. and then kept at 82° C. for 12 hr. The solution was then cooled in an ice bath, and at 15° C. or lower was made alkaline by gradual addition of 1 ml. of sodium hydroxide (2 g. in 10 ml. of water). An additional 10 ml. of water was added and then 30 ml. of methylene chloride. The mixture was shaken and the resulting phases were separated and the aqueous layer was again extracted with 30 ml. of methylene chloride. The combined organic extracts were dried with sodium sulfate and concentrated under reduced pressure to leave the product as a thick oil. The product NMR spectrum (CDCl$_3$) indicated 2 vinyl protons at 6.2 ppm [(CH$_3$)$_4$ Si reference]; R$_F$, 0.47 (10% ethanol in methylene chloride, SiO$_2$), and the molecular ion (mass spectrum) was in agreement.

EXAMPLE 5

A mixture of 250 parts of 4-(4-hydroxy-1-piperidinyl)-3-[(4-hydroxy-1-piperidinyl)methyl]butan-2-one dihydrochloride and 25 parts of lactose is granulated with suitable water, and to this is added 100 parts of maize starch. The mass is passed through a 16 mesh screen. The granules are dried at a temperature below 60° C. The dry granules are passed through a 16 mesh screen and mixed with 3.8 parts of magnesium stearate. They are then compressed into tablets suitable for oral administration.

Using the same ingredients and procedures described above, but substituting for the butan-2-one as active ingredient the following compound: 3,3'-[1,3-propanediylbis (4,1-piperidinediyl)bis(methylene)]bis[3-buten-2-one], there are prepared tablets suitable for oral administration.

The compound used in the foregoing example may be replaced by 25, 100, 250 or 500 parts of piperidino butan-2-ones of this invention to produce tablets suitable for oral administration as an antiinflammatory, antipyretic and/or analgesic according to the method of this invention.

EXAMPLE 6

A mixture of 50 parts of 3-diethylaminomethyl-4-(4-hydroxypiperidino)butan-2-one pamoate, 3 parts of the calcium salt of lignin sulphonic acid, and 273 parts of water is ball-milled until the size of substantially all particles of the compound are less than 10 microns. The suspension is diluted with a solution containing 3 parts of sodium carboxymethylcellulose and 0.9 parts of the butyl ester of p-hydroxy-benzoic acid in 300 parts of water. There is thus obtained an aqueous suspension suitable for oral administration for therapeutic purposes.

EXAMPLE 7

A mixture of 250 parts of 1,1-bis (piperidinomethyl)-propan-2-one succinate, 200 parts of maize starch and 30 parts of alginic acid is mixed with a sufficient quantity of a 10% aqueous paste of maize starch, and granulated. The granules are dried in a current of warm air and the dry granules are then passed through a 16-mesh screen, mixed with 6 parts of magnesium stearate and compressed into tablet form to obtain tablets suitable for oral administration.

EXAMPLE 8

A mixture of 500 parts 3-[(4-isopropylpiperidino)methyl]-4-(4-isopropylpiperidino)butan-2-one dihydrochloride, 60 parts maize starch and 20 parts of gum acacia is granulated with a sufficient quantity of water. The mass is passed through a 12-mesh screen and the granules are dried in a current of warm air. The dry granules are passed through a 16-mesh screen, mixed with 5 parts of magnesium stearate and compressed into tablet form suitable for oral administration.

EXAMPLE 9

(1) Tablets —10,000 scored tablets for oral use, each containing 100 mg. of piperidino-butan-2-one, are prepared from the following ingredients:

|  | Gm. |
|---|---|
| 3-[(3-carbamylpiperidino)methyl]-4-(3-carbamyl-piperidino)butan-2-one adipate | 1000 |
| Starch, U.S.P. | 350 |
| Talc, U.S.P. | 250 |
| Calcium stearate | 35 |

The powdered adipate salt is granulated with a 4% w./v. aqueous solution of methylcellulose U.S.P. (1500 cps.). To the dried granules is added a mixture of the remainder of the ingredients and the final mixture compressed into tablets of proper weight.

(2) Capsules—10,000 two-piece hard gelatin capsules for oral use, each containing 50 mg. of the butan-2-one adipate are prepared from the following ingredients:

|  | Gm. |
|---|---|
| 3-[(3-carbamylpiperidino)methyl]-4-(3-carbamyl-piperidino)butan-2-one adipate | 500 |
| Lactose, U.S.P. | 1000 |
| Starch, U.S.P. | 300 |
| Talc, U.S.P. | 65 |
| Calcium stearate | 25 |

The powdered adipate salt is mixed with the starch-lactose mixture followed by the talc and calcium stearate. The final mixture is then encapsulated in the usual manner. Capsules containing 10 and 25 mg. of the adipate salt are also prepared by substituting 100 and 250 gm. for 500 gm. in the above formulation.

(3) Soft elastic capsules—One piece soft elastic capsules for oral use, each containing 50 mg. of 3-[(3-carbamylpiperidino)methyl]-4-(3-carbamylpiperidino)butan-2-one adipate are prepared in the usual manner by first dispersing the powdered active material in sufficient corn oil to render the material capsulatable.

(4) Aqueous suspension—An aqueous suspension for oral use containing in each 5 ml., 200 mg. of piperidino-butan-2-one, is prepared from the following ingredients:

|  | Gm. |
|---|---|
| 3-[(3-carbamylpiperidino)methyl]-4-(3-carbamyl-piperidino)butan-2-one adipate | 400 |
| Methylparaben, U.S.P. | 7.5 |
| Propylparaben, U.S.P. | 2.5 |
| Saccharin sodium | 12.5 |
| Glycerin, 3000 ml. |  |
| Tragacanth powder | 10 |
| Orange oil flavor | 10 |
| F.D. and C. orange dye | 7.5 |
| Deionized water, q.s. to 10,000 gm. |  |

What is claimed is:

1. A method of treating a condition exhibiting at least one of the symptoms of pain, fever, and inflammation, comprising administering to a patient in need of such treatment a therapeutically effective amount of a compound of the formula:

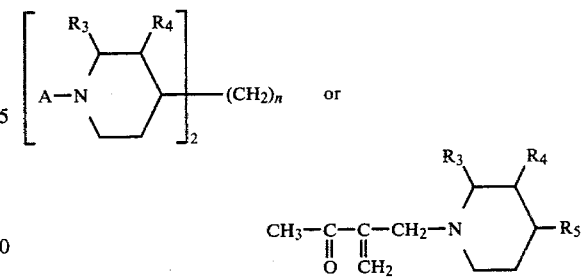

wherein
$R_1$ and $R_2$ are independently selected from hydrogen; $C_{1-8}$ alkyl; $C_{2-8}$ alkenyl; hydroxy $C_{1-8}$ alkyl; and cyclo $C_4$- alkyl; or $R_1$ and $R_2$ taken together with the nitrogen atom form a five- or six-membered saturated heterocyclic ring substituted at the 2-, 3-, and 4-position with $R_3$, $R_4$, and $R_5$, respectively; and $R_3$, $R_4$, and $R_5$ are selected from hydrogen; $C_{1-3}$ alkyl; $C_{2-3}$ alkenyl; hydroxy; hydroxy $C_{1-3}$ alkyl; phenyl; carboxyl; carboxamido; $C_{1-4}$ alkyl N-mono- and N,N-disubstituted carbonylamino; $C_{1-4}$ alkoxycarbonyl; 1-pyrrolidinyl; and 1-piperidinyl; A is

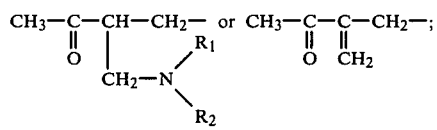

and n is 0 to 3; and acid addition and quaternary salts thereof.

2. The method of claim 1 wherein the compound is 3-(1-piperidinylmethyl)-3-buten-2-one.

3. The method of claim 1 wherein the compound is 3,3'-[1,3-propanediylbis (4,1-piperidinediyl)bis(methylene)]bis [3-buten-2-one].

4. A pharmaceutical composition for treating a condition exhibiting at least one of the symptoms of pain, fever, and inflammation, in unit dosage form suitable for oral administration selected from the group consisting of tablets, oily suspensions, soft and hard gelatin capsules, syrups, and elixirs, comprising a pharmaceutically acceptable, non-toxic carrier, containing one or more agents selected from the group consisting of sweeting agents, flavoring agents, coloring agents, and preserving agents, and a therapeutically effective amount of a compound of the formula:

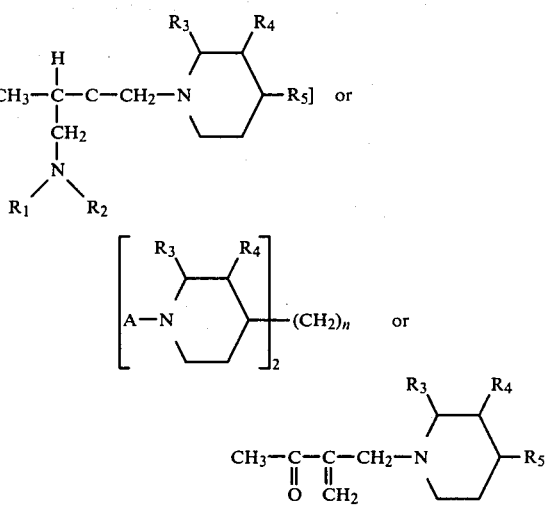

wherein
$R_1$ and $R_2$ are independently selected from hydrogen; $C_{1-8}$ alkyl; $C_{2-8}$ alkenyl; hydroxy $C_{1-8}$ alkyl; and cyclo $C_{4-8}$ alkyl; or $R_1$ and $R_2$ taken together with the nitrogen atom form a five- or six-membered saturated heterocyclic ring substituted at the 2-, 3-, and 4-position with $R_3$, $R_4$ and $R_5$, respectively; and $R_3$, $R_4$, and $R_5$ are selected from hydrogen; $C_{1-3}$ alkyl; $C_{2-3}$ alkenyl; hydroxy; hydroxy $C_{1-3}$ alkyl; phenyl; carboxyl; carboxamido; $C_{1-4}$ alkyl N-mono- and N,N-disubstituted carbonylamino; $C_{1-4}$ alkoxycarbonyl; 1-pyrrolidinyl; and 1-piperidinyl;
A is

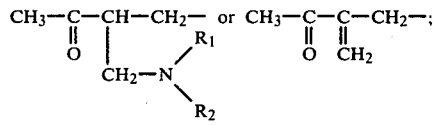

and n is 0 to 3; and acid addition and quaternary salts thereof.

5. The composition of claim 4 wherein the composition is 3-(1-piperidinylmethyl)-3-buten-2-one.

6. The composition of claim 4 wherein the compound is 3,3'-[1,3-propanediylbis (4,1-piperidinediyl)-bis(methylene)]bis[3-buten-2one].

* * * * *